United States Patent
Liang et al.

(10) Patent No.: US 12,188,913 B1
(45) Date of Patent: Jan. 7, 2025

(54) IN-SITU OBSERVATION DEVICE FOR GAS HYDRATES

(71) Applicant: Ningbo Institute of Dalian University of Technology, Ningbo (CN)

(72) Inventors: Huiyong Liang, Pizhou (CN); Xin Lv, Beijing (CN); Shi Shen, Liaoyang (CN); Lei Yang, Dalian (CN); Xingyu Lu, Qingxu (CN); Linan Zhao, Beipiao (CN); Shuangqing Zhang, Hefei (CN)

(73) Assignee: Ningbo Institute of Dalian University of Technology, Ningbo (CN)

( * ) Notice: Subject to any disclaimer, the term of this patent is extended or adjusted under 35 U.S.C. 154(b) by 0 days.

(21) Appl. No.: 18/806,721

(22) Filed: Aug. 16, 2024

(30) Foreign Application Priority Data

Oct. 25, 2023 (CN) .......................... 202311390098.1

(51) Int. Cl.
  *G01N 33/00*  (2006.01)
(52) U.S. Cl.
  CPC ................................ *G01N 33/0011* (2013.01)
(58) Field of Classification Search
  CPC .... G01N 33/0011; G01N 21/01; G01N 21/84; B01J 10/00
  See application file for complete search history.

(56) References Cited

U.S. PATENT DOCUMENTS

2022/0298891 A1* 9/2022 Li ...................... E21B 41/0099

FOREIGN PATENT DOCUMENTS

| CN | 1440832   | A | * | 9/2003  |             |
|----|-----------|---|---|---------|-------------|
| CN | 101298032 | A | * | 11/2008 |             |
| CN | 106000229 | A | * | 10/2016 | ........ B01J 10/00 |
| CN | 207689470 | U | * | 8/2018  | ........ G01N 33/22 |
| CN | 111672423 | A | * | 9/2020  |             |

OTHER PUBLICATIONS

CN-101298032-A (Year: 2008).*
CN-106000229-A (Year: 2016).*
CN-111672423-A (Year: 2003).*
CN-1440832-A (Year: 2020).*
CN-207689470-U (Year: 2018).*

* cited by examiner

*Primary Examiner* — Kristina M Deherrera
*Assistant Examiner* — Fatemeh Esfandiari Nia

(57) ABSTRACT

An in-situ observation device for gas hydrates includes a reactor, which includes a visual tube, a pulling rod, a temperature-controlled seed crystal rod and a spiral adjuster. An upper end and a lower end of the visual tube are respectively equipped with an upper end cap and a lower end cap. The upper end cap defines an air inlet, and the lower end cap defines a liquid inlet. An upper end of the temperature-controlled seed crystal rod is connected to an adjusting flange. The adjusting flange is connected to the spiral adjuster. A lower end of the temperature-controlled seed crystal rod hermetically passes through the upper end cap and is located in the visual tube. The temperature-controlled seed crystal rod defines a cooling liquid channel, and a cooling liquid inlet and a cooling liquid outlet, a seed crystal rod liquid inlet and a seed crystal rod outlet.

7 Claims, 4 Drawing Sheets

IN-SITU OBSERVATION DEVICE FOR GAS HYDRATES

TECHNICAL FIELD

The present disclosure relates to the field of gas hydrate's technologies, and particularly to an in-situ observation device for gas hydrates and method of use thereof.

BACKGROUND

Gas hydrates are ice-like solid compounds with a cage-like structure, formed by water and small molecular gases such as methane ($CH_4$), ethane ($C_2H_6$), carbon dioxide ($CO_2$), and hydrogen ($H_2$). Hydrates have a high gas storage capacity and good gas storage stability. In addition, the hydrates possess characteristics such as high latent heat of phase transition. The applications of hydrate technology have attracted widespread attention in the energy and environmental fields due to excellent properties of the hydrates and the applications of hydrate technology mainly include hydrate energy storage, natural gas hydrate exploitation, gas separation, carbon dioxide capture and geological sequestration in the form of hydrates, seawater desalination, hydrate cold storage, and so on. The applications of hydrate technology all involve the issue of hydrate formation. The rate of hydrate formation is a major factor affecting the large-scale industrial application of hydrate technology. Researches into the hydrate formation process help to deeply understand the factors controlling the rate of hydrate formation, providing guidance for the development and application of hydrate technology.

The hydrate crystal morphology is an external reflection of its internal structure and is largely influenced by various environmental factors involved in its growth process, such as temperature, pressure, flow conditions, additives, and impurities. The hydrate crystal morphology can reflect both internal and external factors affecting the hydrate growth process. Therefore, studying the growth morphology of hydrate crystals helps to understand the kinetic mechanism of hydrate growth, providing a theoretical basis for the applications of hydrate technology.

However, the gas hydrate tends to form a layer of hydrate film at the gas-liquid interface first. The formed hydrate film separates the gas phase and the liquid phase (i.e., aqueous phase), creating a mass transfer barrier. Subsequently, the growth of hydrates mainly occurs through the thickening of the hydrate film. Currently, there is a lack of observation devices for the growth morphology of hydrate crystals, especially for the growth of hydrate crystals in solution.

SUMMARY

In order to overcome the problems of the related art, the present disclosure provides an in-situ observation device for gas hydrates, to achieve observation of the growth morphology of hydrate crystals especially the growth morphology of hydrate crystals in the solution.

The present disclosure provides an in-situ observation device for gas hydrates, including: a reactor; where the reactor includes a visual tube, a pulling rod, a temperature-controlled seed crystal rod and a spiral adjuster; an upper end and a lower end of the visual tube are respectively equipped with an upper end cap and a lower end cap, and the upper end cap and the lower end cap are connected to the pulling rod; the upper end cap defines an air inlet, and the lower end cap defines a liquid inlet; an upper end of the temperature-controlled seed crystal rod is connected to an adjusting flange through an adjusting rod; the adjusting flange is connected to the spiral adjuster, and the adjusting flange is connected to the pulling rod; an lower end of the temperature-controlled seed crystal rod hermetically passes through the upper end cap and is located in the visual tube; the temperature-controlled seed crystal rod defines a cooling liquid channel, and a cooling liquid inlet and a cooling liquid outlet which are connected to the cooling liquid channel; and the temperature-controlled seed crystal rod defines a seed crystal rod liquid inlet and a seed crystal rod outlet.

In an embodiment, the upper end of the visual tube is connected to the upper end cap through an upper end cap sleeve.

In an embodiment, the lower end of the visual tube is connected to the lower end cap through a lower end cap sleeve.

In an embodiment, the upper end cap is connected to the pulling rod through an upper end cap positioning nut.

In an embodiment, the lower end cap is connected to the pulling rod through a lower end cap positioning nut.

In an embodiment, the adjusting flange is connected to the pulling rod through a cooperation of an adjusting flange positioning nut and an adjusting flange nut.

In an embodiment, the upper end of the temperature-controlled seed crystal rod is connected to the adjusting rod through a connecting cap.

In an embodiment, the in-situ observation device for gas hydrates further includes: a transparent water bath, a first circulating water bath, a gas injection pump, a liquid injection pump, a vacuum pump, a gas cylinder, a camera, a computer, and a second circulating water bath.

The reactor is disposed in the transparent water bath; the first circulating water bath is connected to the transparent water bath individually through a first circulation water pipe and a second circulation water pipe; the vacuum pump is connected to the air inlet through a first pipeline, and the gas cylinder is connected to the air inlet through a second pipeline; the gas injection pump is located on the second pipeline, and the liquid injection pump is connected to the liquid inlet through a third pipeline; the second circulating water bath is connected to the cooling liquid inlet and the cooling liquid outlet through a third circulation water pipe and a fourth circulation water pipe; the camera is located on a side of the transparent water bath, a signal output terminal of the camera is connected to a signal input terminal of the computer.

Further, the in-situ observation device for gas hydrates further includes a pressure sensor; the pressure sensor is located on the second pipeline, and a signal output terminal of the pressure sensor is connected to the signal input terminal of the computer.

Further, the in-situ observation device for gas hydrates further includes a temperature sensor; a sensing terminal of the temperature sensor is located in the transparent water bath, and a signal output terminal of the temperature sensor is connected to the signal input terminal of the computer.

The present disclosure at least has the following advantages and beneficial effects.

The present disclosure is capable of adjusting the height of the temperature-controlled seed crystal rod through the spiral adjuster, ensuring that the hydrate seed crystals at the seed crystal rod outlet are completely submerged below the liquid surface, allowing for the observation of the growth of hydrate crystals in the aqueous solution.

BRIEF DESCRIPTION OF DRAWINGS

In the drawings, which are not necessarily drawn to scale, reference numerals may be used to identify similar elements in different views. Reference numerals with letter suffixes or different letter suffixes may indicate different instances of similar elements. The drawings are generally citing examples rather than limiting to illustrate various embodiments and are used in conjunction with the specification and the claims to explain various embodiments of the present disclosure. When appropriate, the same reference numerals are used throughout the drawings to refer to the same or similar parts. Such embodiments are exemplary and are not intended to be exhaustive or exclusive embodiments of the apparatus or method described herein.

Figure 1:
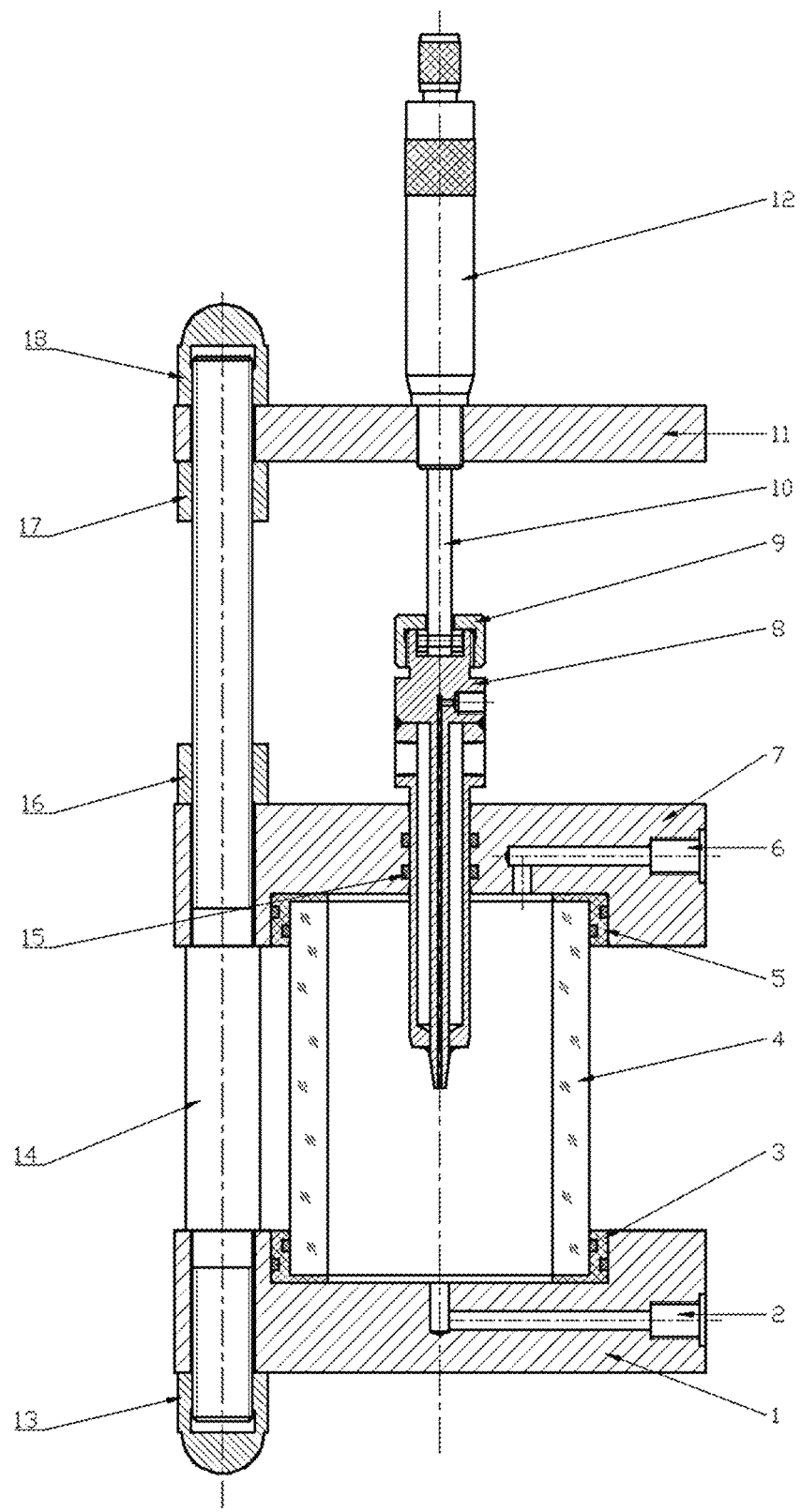
FIG. 1 illustrates a schematic structural diagram of a reactor of an in-situ observation device for gas hydrates according to an embodiment of the present disclosure.
Figure 2:
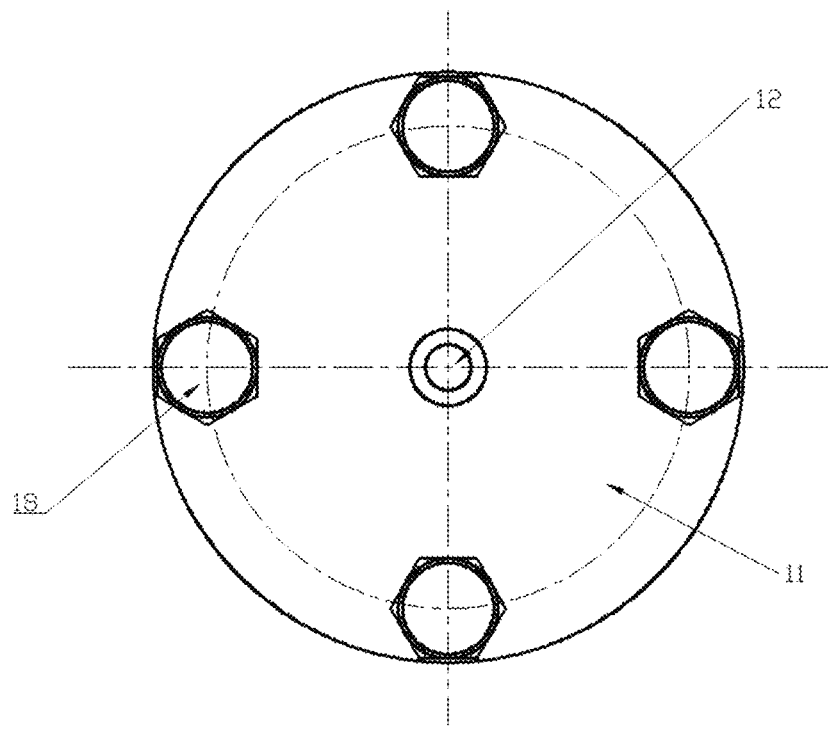
FIG. 2 illustrates a top view of the reactor of the in-situ observation device for gas hydrates according to the embodiment of the present disclosure.
Figure 3:
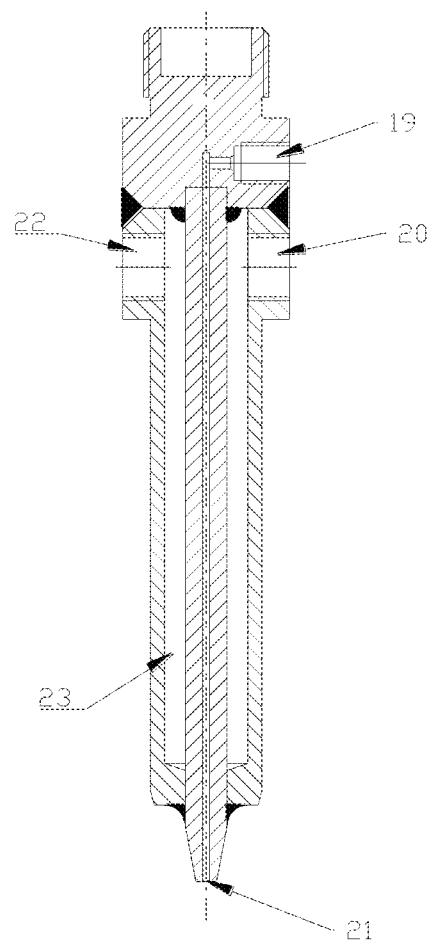
FIG. 3 illustrates a sectional view of a temperature-controlled seed crystal rod of the in-situ observation device for gas hydrates according to the embodiment of the present disclosure.
Figure 4:
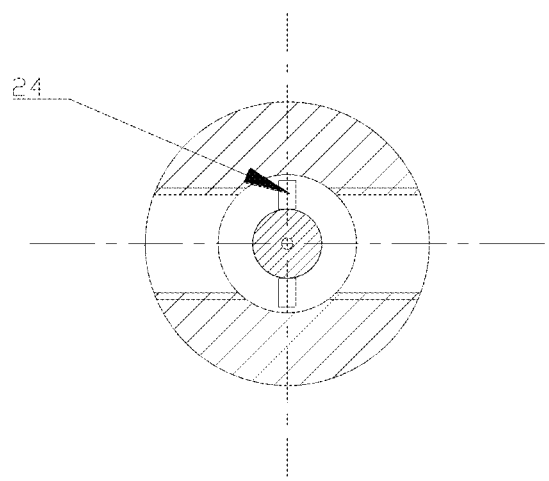
FIG. 4 illustrates a sectional view of a position of a seed crystal rod inlet of the temperature-controlled seed crystal rod of the in-situ observation device for gas hydrates according to the embodiment of the present disclosure.

Description of reference numerals: 1 lower end cap; 2 liquid inlet; 3 lower end cap sleeve; 4 visual tube; 5 upper end cap sleeve; 6 air inlet; 7 upper end cap; 8 temperature-controlled seed crystal rod; 9 connecting cap; 10 adjusting rod; 11 adjusting flange; 12 spiral adjuster; 13 lower end cap positioning nut; 14 pulling rod; 15 seal ring; 16 upper end cap positioning nut; 17 adjusting flange positioning nut; 18 adjusting flange nut; 19 seed crystal rod liquid inlet; 20 cooling liquid inlet; 21 seed crystal rod outlet; 22 cooling liquid outlet; 23 cooling liquid channel; 24 baffle plate; 25 transparent water bath; 26 first circulating water bath; 27 gas injection pump; 28 liquid injection pump; 29 vacuum pump; 30 gas cylinder; 31 camera; 32 computer; 33 second circulating water bath; 34 reactor; 35 first circulation water pipe; 36 second circulation water pipe; 37 first pipeline; 38 second pipeline; 39 third pipeline; 40 third circulation water pipe; 41 fourth circulation water pipe; 42 pressure sensor; 43 temperature sensor.

DETAILED DESCRIPTION OF EMBODIMENTS

To better enable those skilled in the art to understand the technical solution of the present disclosure, the following detailed description is provided in conjunction with the accompanying drawings and specific embodiments, but without limiting the present disclosure. If the various steps described herein are not necessarily in a particular order, the order in which they are described as examples should not be construed as limiting. Those skilled in the art should know that the order can be adjusted as long as the logical relationship between them is not destroyed, which would otherwise prevent the entire process from being implemented.

The present disclosure provides an in-situ observation device for gas hydrates, including: a reactor 34. As illustrated in FIGS. 1, 2, 3 and 4, the reactor 34 includes a visual tube 4, a pulling rod 14, a temperature-controlled seed crystal rod 8 and a spiral adjuster 12. An upper end of the visual tube 4 and a lower end of the visual tube 4 are respectively equipped with an upper end cap 7 and a lower end cap 1, and the upper end cap 7 and the lower end cap 1 are connected to the pulling rod 14. The upper end cap 7 defines an air inlet 6, and the lower end cap 1 defines a liquid inlet 2. An upper end of the temperature-controlled seed crystal rod 8 is connected to an adjusting flange 11 through an adjusting rod 10. The adjusting flange 11 is connected to the spiral adjuster 12, and the adjusting flange 11 is connected to the pulling rod 14. A lower end of the temperature-controlled seed crystal rod 8 hermetically passes through the upper end cap 7 and is located in the visual tube 4. The temperature-controlled seed crystal rod 8 defines a cooling liquid channel 23, and a cooling liquid inlet 20 and a cooling liquid outlet 22 which are connected to the cooling liquid channel. The temperature-controlled seed crystal rod 8 defines a seed crystal rod liquid inlet 19 and a seed crystal rod outlet 21.

In an embodiment, an interior of the visual tube 4 can be vacuumized through the air inlet 6. The lower end of the temperature-controlled seed crystal rod 8 can be connected to the upper end cap 7 via a seal ring 15, allowing the temperature-controlled seed crystal rod 8 to be hermetically passed through the upper end cap 7 and located in the visual tube 4. Experimental liquid can be pumped into the visual tube 4 through the liquid inlet 2 defined on the lower end cap 1. The cooling liquid channel 23 on the temperature-controlled seed crystal rod 8 can be circulated with cooling water to maintain a constant temperature control of the temperature-controlled seed crystal rod 8. The spiral adjuster 12 is configured to adjust a height of the temperature-controlled seed crystal rod 8. The adjusting flange 11 is movably connected with the pulling rod 14. By adjusting the spiral adjuster 12, the height of the temperature-controlled seed crystal rod 8 is adjusted so that hydrate seed crystals at a position of a seed crystal rod outlet 21 of the temperature-controlled seed crystal rod 8 is completely submerged below a liquid surface, thereby observing growths of hydrate crystals in an aqueous solution.

In a specific embodiment, the upper end of the visual tube 4 is connected to the upper end cap 7 through an upper end cap sleeve 5. The lower end of the visual tube 4 is connected to the lower end cap 1 through a lower end cap sleeve 3.

In a specific embodiment, the upper end cap 7, the lower end cap 1, and the adjusting flange 11 are adjustably connected to the pulling rod 14. Specifically, the upper end cap 7 is connected to the pulling rod 14 via an upper end cap positioning nut 16, the lower end cap 1 is connected to the pulling rod 14 via a lower end cap positioning nut 13, and the adjusting flange 11 is connected to the pulling rod 14 by a cooperation of an adjusting flange positioning nut 17 and an adjusting flange nut 18.

In a specific embodiment, the upper end of the temperature-controlled seed crystal rod 8 is connected to the adjusting rod 10 through a connecting cap 9.

In a specific embodiment, a baffle plate 24 can be placed in the seed crystal rod liquid inlet 19 defined on the temperature-controlled seed crystal rod 8.

Figure 5:
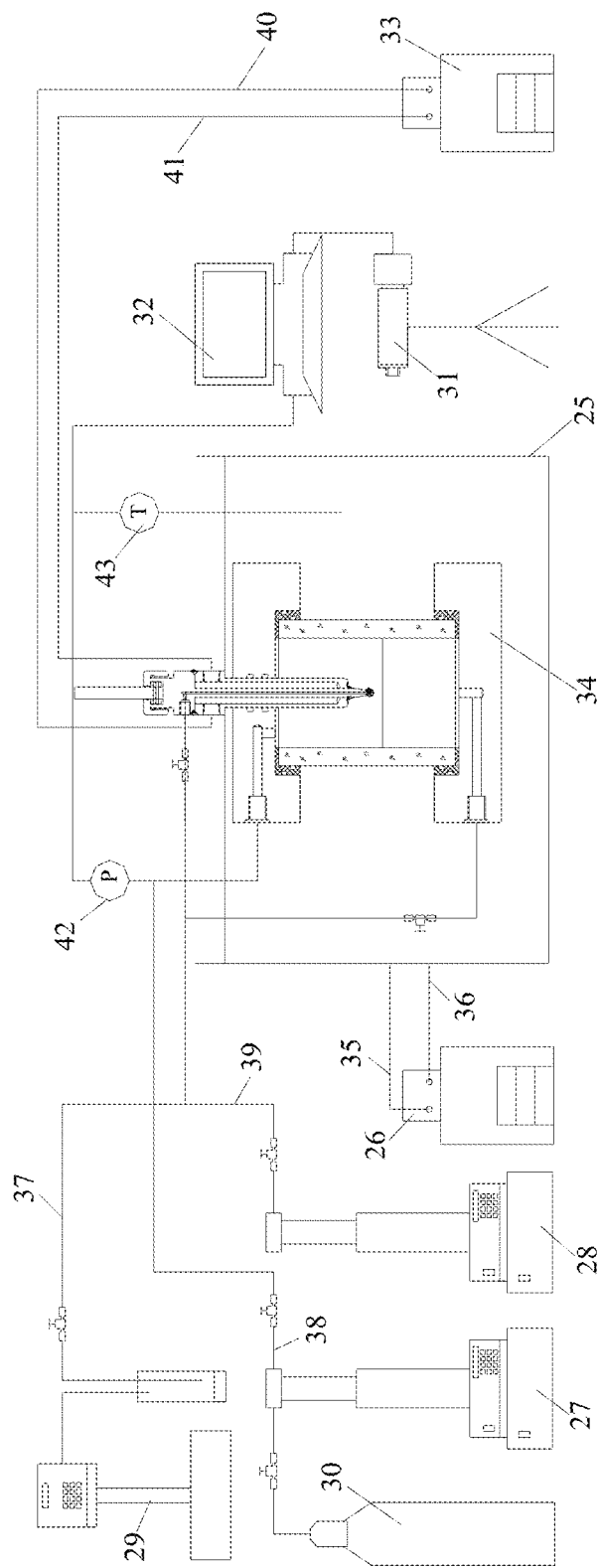
FIG. 5 illustrates a schematic diagram of an entire mechanism of the in-situ observation device for gas hydrates according to the embodiment of the present disclosure.

In a specific embodiment, as illustrated in FIG. 5, the in-situ observation device for gas hydrates further includes: a transparent water bath 25, a first circulating water bath 26, a gas injection pump 27, a liquid injection pump 28, a vacuum pump 29, a gas cylinder 30, a camera 31, a computer 32, and a second circulating water bath 33. The reactor 34 is disposed in the transparent water bath 25. The first circulating water bath 26 is connected to the transparent water bath 25 through a first circulation water pipe 35 and a second circulation water pipe 36. The vacuum pump 29 is connected to the air inlet 6 through a first pipeline 37. The gas cylinder 30 is connected to the air inlet 6 through a second pipeline 38. The gas injection pump 27 is located on the second pipeline 38, and the liquid injection pump 28 is connected to the liquid inlet 2 through a third pipeline 39. The second circulating water bath 33 is connected to the cooling liquid inlet 20 and the cooling liquid outlet 22 through a third circulation water pipe 40 and a fourth circulation water pipe 41. The camera 31 is located on a side of the transparent water bath 25, and a signal output terminal of the camera 31 is connected to a signal input terminal of a computer 32.

More specifically, the in-situ observation device for gas hydrates further includes a pressure sensor 42 and a temperature sensor 43. The pressure sensor 42 is located on the second pipeline 38, and a signal output terminal of the pressure sensor 42 is connected to the signal input terminal of the computer 32. A sensing terminal of the temperature sensor 43 is located in the transparent water bath 25, and a signal output terminal of the temperature sensor 43 is connected to the signal input terminal of the computer 32.

A method of using the in-situ observation device for gas hydrates as illustrated in FIG. 5 includes following steps S1 to S8.

S1, a hydrate crystal growth reactor (also referred to as the reactor) is placed in the transparent water bath, experimental pipes are connected.

S2, the reactor is vacuumized by using the vacuum pump, removing air in the reactor.

S3, experimental gas is injected into the reactor using the gas injection pump until a gas pressure reaches 0.1 megapascal (MPa).

S4, a certain amount of the experimental liquid is injected into the reactor through the liquid injection pump.

S5, a circulating water bath connected to the transparent water bath (also referred to as the first circulating water bath) is activated to bring a temperature of the transparent water bath to an experimental temperature.

S6, a drop of water is dripped at the position of the seed crystal rod outlet of the seed crystal rod (also referred to as temperature-controlled seed crystal rod) and maintained at the position of the seed crystal rod outlet.

S7, a circulating water bath connected to the seed crystal rod (also referred to as the second circulating water bath) is activated, a setting temperature of the circulating water bath connected to the seed crystal rod is −20° C., causing the water drop at the position of the seed crystal rod outlet to freeze.

S8, after confirming that the water drop at the position of the seed crystal rod outlet has frozen, the environmental gas is injected into the reactor by using the gas injection pump until reaching an experimental pressure.

Then, experiments on hydrate formation at different forms (different interfaces) can be conducted, and the growth morphology of hydrates can be observed and recorded using the camera.

(1) Hydrate Growth Process at a Gas-Solid Interface

The temperature of the circulating water bath connected to the seed crystal rod is adjusted to an experimental temperature (which is still below the freezing point), a hydrate growth at the gas-ice interface is observed.

(2) Hydrate Growth Process at a Gas-Liquid Interface

The temperature of the circulating water bath connected to the seed crystal rod is adjusted to an experimental temperature (which is above the freezing point), and a hydrate growth at the gas-liquid interface is observed.

(3) Hydrate Crystal Growth in an Aqueous Solution

After confirming that hydrate seed crystals have formed on a surface of an ice ball at the position of the seed crystal rod outlet, the temperature of the circulating water bath connected to the seed crystal rod is adjusted to an experimental temperature. By adjusting a height of the seed crystal rod with the spiral adjuster, the hydrate seed crystals at the position of the seed crystal rod outlet are completely submerged below the liquid surface, and the growth of hydrate crystals in the aqueous solution is observed.

The above description is merely preferred specific embodiments of the present disclosure, but the scope of protection of the present disclosure is not limited to these. Any one of those skilled in the art may make equivalent substitutions or modifications within the technical scope disclosed by the present disclosure, based on the technical solution and inventive concept of the present disclosure, which should all fall within the scope of protection of the present disclosure.

What is claimed is:

1. An in-situ observation device for gas hydrates, comprising:
   a reactor; wherein the reactor comprises a visual tube, a pulling rod, a temperature-controlled seed crystal rod and a spiral adjuster; an upper end and a lower end of the visual tube are respectively equipped with an upper end cap and a lower end cap, and the upper end cap and the lower end cap are connected to the pulling rod; the upper end cap defines an air inlet, and the lower end cap defines a liquid inlet; an upper end of the temperature-controlled seed crystal rod is connected to an adjusting flange through an adjusting rod; the adjusting flange is connected to the spiral adjuster, and the adjusting flange is connected to the pulling rod; a lower end of the temperature-controlled seed crystal rod hermetically passes through the upper end cap and is located in the visual tube; the temperature-controlled seed crystal rod defines a cooling liquid channel, and a cooling liquid inlet and a cooling liquid outlet which are connected to the cooling liquid channel; and the temperature-controlled seed crystal rod defines a seed crystal rod liquid inlet and a seed crystal rod outlet;
   wherein the in-situ observation device for gas hydrates further comprises: a transparent water bath, a first circulating water bath, a gas injection pump, a liquid injection pump, a vacuum pump, a gas cylinder, a camera, a computer, and a second circulating water bath; the reactor is disposed in the transparent water bath; the first circulating water bath is connected to the transparent water bath individually through a first circulation water pipe and a second circulation water pipe; the vacuum pump is connected to the air inlet through a first pipeline, and the gas cylinder is connected to the air inlet through a second pipeline; the gas injection pump is located on the second pipeline, and the liquid injection pump is connected to the liquid inlet through a third pipeline; the second circulating water bath is connected to the cooling liquid inlet and the cooling liquid outlet through a third circulation water pipe and a fourth circulation water pipe; and the camera is located on a side of the transparent water bath, and a signal output terminal of the camera is connected to a signal input terminal of the computer;
   wherein the in-situ observation device for gas hydrates further comprises: a pressure sensor located on the second pipeline, and a signal output terminal of the pressure sensor is connected to the signal input terminal of the computer; and wherein the in-situ observation device for gas hydrates further comprises: a temperature sensor; a sensing terminal of the temperature sensor is located in the transparent water bath, and a signal output terminal of the temperature sensor is connected to the signal input terminal of the computer.

2. The in-situ observation device for gas hydrates as claimed in claim 1, wherein the upper end of the visual tube is connected to the upper end cap through an upper end cap sleeve.

3. The in-situ observation device for gas hydrates as claimed in claim 1, wherein the lower end of the visual tube is connected to the lower end cap through a lower end cap sleeve.

4. The in-situ observation device for gas hydrates as claimed in claim 1, wherein the upper end cap is connected to the pulling rod through an upper end cap positioning nut.

5. The in-situ observation device for gas hydrates as claimed in claim 1, wherein the lower end cap is connected to the pulling rod through a lower end cap positioning nut.

6. The in-situ observation device for gas hydrates as claimed in claim 1, wherein the adjusting flange is connected to the pulling rod through a cooperation of an adjusting flange positioning nut and an adjusting flange nut.

7. The in-situ observation device for gas hydrates as claimed in claim 1, wherein the upper end of the temperature-controlled seed crystal rod is connected to the adjusting rod through a connecting cap.

\* \* \* \* \*